June 30, 1970 F. W. ANDERSON Plant Pat. 2,976
NECTARINE TREE
Filed Sept. 30, 1968
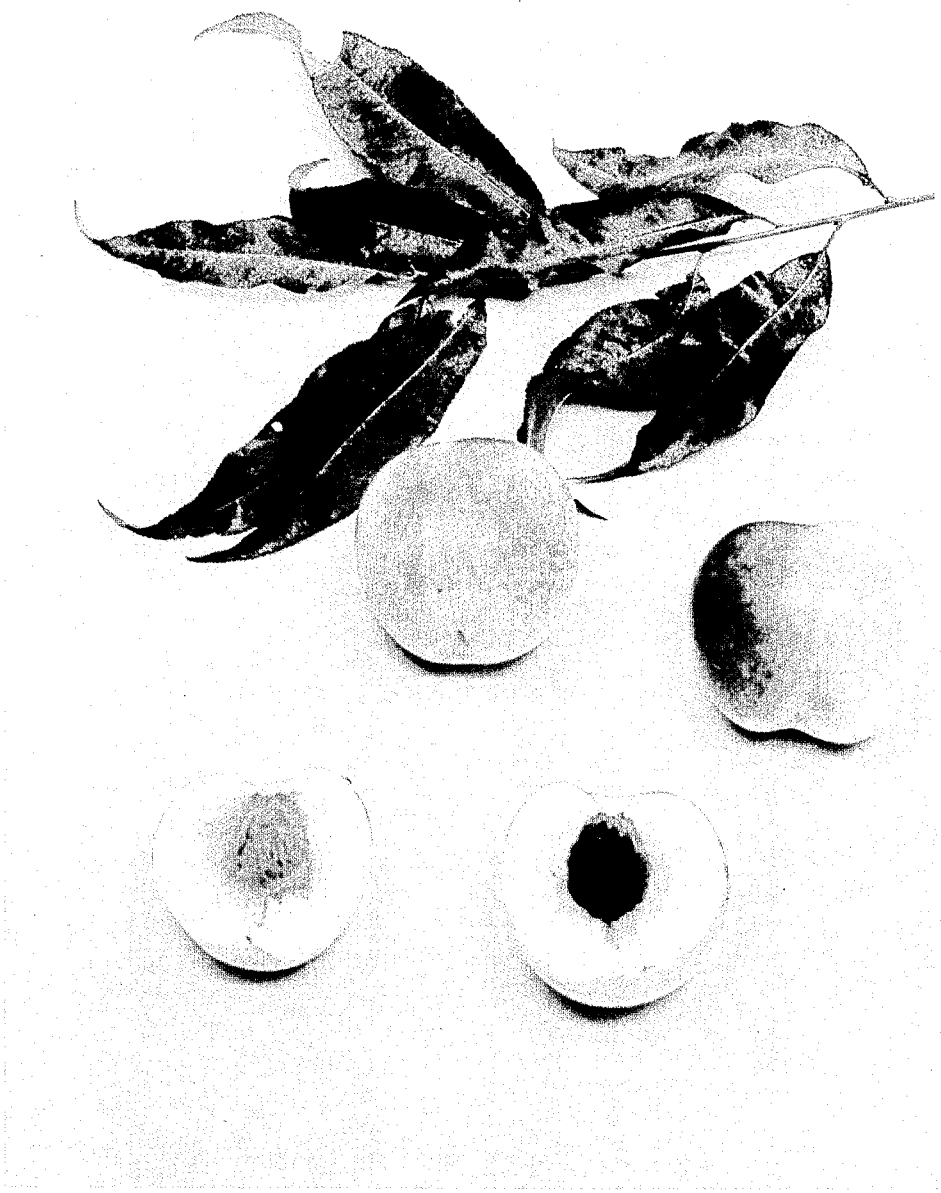
INVENTOR
Frederic W. Anderson
BY
Webster & Webster
ATTORNEYS United States Patent Office Plant Pat. 2,976
Patented June 30, 1970

2,976
NECTARINE TREE

Frederic W. Anderson, Merced, Calif., assignor to Reedley Nursery, Inc., Reedley, Calif., a corporation of California Filed Sept. 30, 1968, Ser. No. 763,991
Int. Cl. A01h 5/03
U.S. Cl. Plt.—41 1 Claim

ABSTRACT OF THE DISCLOSURE

A variety of nectarine tree which is large, spreading, and a regular and productive bearer of large, late-season freestone fruit having firm yellow flesh, and yellow skin substantially overspread with red.

BACKGROUND OF THE VARIETY

Over a substantial number of years I have engaged in an extensive and continuing plant breeding program at my experimental nursery and orchard located near Le Grand, Merced County, Calif.; one purpose of such program being to provide improved varieties of fruit trees. The present variety of nectarine tree resulted from my endeavors in the conduct of such plant breeding program.

ORIGIN OF THE VARIETY

The herein claimed new and distinct variety of nectarine tree was originated by me in my experimental orchard located as aforesaid, in the following manner:

Seeds obtained from a cross of the Sun Grand (U.S. Plant Pat. No. 974) nectarine by an unnamed seedling of the Gold King (U.S. Plant Pat. No. 1,424) nectarine were planted, and the resultant seedlings maintained under careful and continuing observation.

When such first-generation seedlings bore fruit, one—and which is the instant variety—evidenced novel and commercially desirable characteristics, and was, therefore, selected by me for asexual reproduction, preparatory to introduction to the trade.

ASEXUAL REPRODUCTION OF THE VARIETY

Subsequent to origination and selection by me of the present variety of nectarine tree, in the manner above described, I asexually reproduced it by top-working on mature nectarine trees in my said experimental orchard, and in maturity such reproductions ran true to the original tree in all respects.

SUMMARY OF THE VARIETY

The herein claimed variety of nectarine tree is large and sperading in growth, and a regular and productive bearer of large freestone fruit having firm yellow flesh, and yellow skin substantially overspread with red; the variety being distinctively characterized by its firm fruit which enhances shipping quality, and by a late-season ripening period approximately three weeks after the freestone Golden Grand (U.S. Plant Pat. No. 1,324) nectarine and about one week later than the clingstone Regal Grand (U.S. Plant Pat. No. 1,751) nectarine.

The present variety bears fruit which is the latest ripening in a series of nectarine trees which I have originated in order to extend the shipping season of freestone nectarines beyond that of the Sun Grand.

BRIEF DESCRIPTION OF THE DRAWING

The drawing is an illustration, by photographic reprotion in color, of fruit and leaves of the variety; one fruit being cut in half to expose and show the flesh, and with the stone remaining in place in one of such halves.

DESCRIPTION OF THE VARIETY

The botanical details of this new and distinct variety of nectarine tree—with color definitions referenced to Maerz and Paul Dictionary of Color—are as follows:

Tree:
- *Size.*—Large.
- *Vigor.*—Vigorous.
- *Growth.*—Spreading.
- *Production.*—Productive.
- *Bearing.*—Regular bearer.

Trunk:
- *Size.*—Medium.
- *Texture.*—Medium.

Branches:
- *Size.*—Medium.
- *Texture.*—Smooth.

Leaves:
- *Size.*—Large. Average length—6½". Average width—1¾".
- *Form.*—Lanceolate.
- *Thickness.*—Medium.
- *Texture.*—Smooth.
- *Margin.*—Crenate.
- *Petiole.*—Medium length—average ½". Medium thickness.
- *Glands.*—Number and position—usually 2 on blade, and 2 to 4 on petiole. Alternate; medium size; reniform.
- *Color.*—Top side—Medium Green (23–L–7). Under side—Lighter Green (22–L–6).

Flower buds:
- *Size.*—Medium.
- *Length.*—Medium.
- *Form.*—Plump.

Flowers:
- *Blooming period.*—About with Sun Grand nectarine. Medium, as compared with other varieties.
- *Size.*—Large; showy.

Fruit:
- *Maturity when described.*—Eating ripe.
- *Date of first picking.*—Sept. 1, 1968.
- *Date of last picking.*—Sept. 10, 1968.
- *Size.*—Uniform; large. Average diameter axially—2½". Average transversely in suture plane—2⅝".
- *Form.*—Uniform; symmetrical; globose to oblong.
- *Suture.*—Shallow. Extends from base to beyond apex, with slight depression beyond pistil point.
- *Ventral surface.*—Rounded slightly.
- *Cavity.*—Circular.
- *Base.*—Truncate.
- *Apex.*—Short; depressed.

Skin:
- *Thickness.*—Medium.
- *Texture.*—Tender.
- *Tendency to crack.*—Slight.
- *Down.*—Wanting.
- *Color.*—Yellow (10–L–5) substantially overspread with Red (5–L–5), streaked and mottled to darker Red (7–J–6).

Flesh:
- *Juice.*—Moderate.
- *Texture.*—Firm; melting
- *Fibers.*—Few; tender.
- *Ripens.*—Evenly.
- *Flavor.*—Subacid; vinous.
- *Aroma.*—Distinct.
- *Eating quality.*—Good.

*Color.*—Yellow (10–K–4). Surface of pit cavity—Red (6–L–3), with red streaked into flesh.

Stone:

*Type.*—Free; parts from flesh smoothly.

*Size.*—Large. Average length—1½". Average breadth—1". Average thickness—¾".

*Form.*—Oblong.

*Base.*—Oblique.

*Hilum.*—Broad.

*Apex.*—Acute.

*Sides.*—Equal.

*Ridges.*—Rounded; interrupted.

*Ventral edge.*—Thick.

*Dorsal edge.*—Full, with shallow groove.

*Tendency to split.*—Slight.

*Color.*—Brown (8–L–7).

Use: Market; dessert; long distance shipping.

Keeping quality: Good.

Shipping quality: Good.

The nectarine tree and its fruit herein described may vary in slight detail due to climatic and soil conditions under which the variety may be grown; the present description being of the variety as grown in the Central Valley of California.

I claim:

1. A new and distinct variety of nectarine tree, substantially as illustrated and described, which is large and spreading in growth, and a regular and productive bearer of large freestone fruit having yellow flesh, and yellow skin substantially overspread with red; the variety being particularly characterized by fruit whose flesh is firm, and by a late-season ripening period of such fruit, and which ripening period is approximately three weeks after the freestone Golden Grand nectarine and about one week later than the clingstone Regal Grand nectarine.

No references cited.

ROBERT E. BAGWILL, Primary Examiner